US00PP24376P2

(12) United States Plant Patent
Suphachadiwong

(10) Patent No.: US PP24,376 P2
(45) Date of Patent: Apr. 8, 2014

(54) ***PHALAENOPSIS* PLANT NAMED 'SUPHAL1109'**

(50) Latin Name: ***Phalaenopsis* hybrid**
Varietal Denomination: SUPHAL1109

(75) Inventor: Thumrong Suphachadiwong, Chonburi (TH)

(73) Assignee: Suphachatwong Innovation Co., Ltd (TH)

( * ) Notice: Subject to any disclaimer, the term of this patent is extended or adjusted under 35 U.S.C. 154(b) by 0 days.

(21) Appl. No.: 13/573,441

(22) Filed: Sep. 14, 2012

(51) Int. Cl.
*A01H 5/00* (2006.01)

(52) U.S. Cl.
USPC ..... Plt./311

(58) Field of Classification Search
USPC ..... Plt./311
See application file for complete search history.

*Primary Examiner* — Kent L Bell
(74) *Attorney, Agent, or Firm* — Cassandra Bright

(57) ABSTRACT

A new and distinct *Phalaenopsis* cultivar named 'SUPHAL1109' is disclosed, characterized by petals and sepals colored bright white with clear red-purple striping. Plants are unusually compact. The new variety is a *Phalaenopsis*, typically produced as an indoor ornamental plant.

1 Drawing Sheet

Latin name of the genus and species: *Phalaenopsis* hybrid. Variety denomination: 'SUPHAL1109'.

BACKGROUND OF THE INVENTION

This application relates to a new cultivar of *Phalaenopsis* hybrid. The new variety is the product of a planned breeding program. The new variety originated as a seedling from the crossing of the unpatented, proprietary seed parent *Phalaenopsis* 'RBB1MR' with the unpatented, proprietary pollen parent referred to as *Phalaenopsis* 'HWVZ1734'. The crossing was made by the inventor in his research greenhouse in Chonburi, Thailand in May of 2005.

The new variety was first selected by the inventor, Thumrong Suphachadiwong, a citizen of Thailand, in August 2008, in a research greenhouse belonging to the inventor in Chonburi, Thailand. After identifying the new variety as a potentially interesting selection, the inventor continued confidential testing and propagation of 'SUPHAL1109', assessing stability of the unique characteristics of this variety.

Asexual reproduction of the new cultivar 'SUPHAL1109' was first performed at a commercial laboratory belonging to the inventor in Chonburi, Thailand by tissue culture in August of 2008. Access to all plants was restricted, as plants were kept in a greenhouse not open to the public, and tissue culture plantlets were in a laboratory belonging to the inventor, and not accessible to the public. Through subsequent propagation, multiple generations have been reproduced, which have shown that the unique features of this cultivar are stable and reproduced true to type.

SUMMARY OF THE INVENTION

The cultivar 'SUPHAL1109' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SUPHAL1109.' These characteristics in combination distinguish 'SUPHAL1109' as a new and distinct *Phalaenopsis* cultivar:

1. Unique bright sepal and petal coloration of white with clear red purple striping.
2. Unusual compact plant shape.

PARENT COMPARISON

Plants of the new cultivar 'SUPHAL1109' are similar to the seed parent, *Phalaenopsis* 'RBB1MR' in most horticultural characteristics. The new variety, however, produces flowers with a different color than the seed parent.

Plants of the new cultivar 'SUPHAL1109' are similar to the pollen parent, *Phalaenopsis* 'HWVZ1734' in most horticultural characteristics. Plants of the new variety, however, are more compact than the pollen parent.

COMMERCIAL COMPARISON

'SUPHAL1109' is similar in most horticultural characteristics to the unpatented commercial variety *Doritaenopsis* 'Happy King Pro' in most horticultural characteristics. The new variety, however, produces sepals and petals with a different color pattern. Additionally, the new variety has a different lip coloration. The lip, petal and sepal shapes are different in the new variety, compared to 'Happy King Pro'.

BRIEF DESCRIPTION OF THE PHOTOGRAPH

The accompanying photograph in FIG. 1 illustrates in full color a typical plant of 'SUPHAL1109' grown in a commercial greenhouse in Zuidbroek, the Netherlands.

This plant is approximately 18 months old, shown planted in an 11 cm container. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001, except where general terms of ordinary dictionary significance are used. The following observations and measurements describe 'SUPHAL1109' plants grown in a greenhouse in Zuidbroek, the Netherlands. Temperatures ranged between 18° C. and 28° C. day and night. No photoperiodic or chemical treatments were given to the plants. During bright Summer conditions, shade was given. During dark Winter months, supplemental light was given at unspecified amounts. Measurements and numerical values represent averages of typical plant types.

Botanical classification: *Phalaenopsis* hybrid 'SUPHAL1109'.

PROPAGATION

Type of propagation typically used: Tissue culture.

Time to initiate roots: About 21 days at approximately 28° C.

Time to produce a rooted cutting/liner: About 26 weeks at approximately 18° C. to 28° C.

Root description: Thick (typical for *Phalaenopsis*) and rounded, average diameter: 5 mm, colored greyed-green; near 198D.

PLANT

Growth habit: Monopodial.

Height from top of soil line to top of foliage: Average 9.1 cm.

Height from top of soil line to top of flowers: Average 29.6 cm.

Plant spread: At widest, average: 29.0 cm; at narrowest: 17.9 cm.

Normal pot size: 11 cm.

Growth rate: Moderate.

Number of leaves per plant: Average 8.

FOLIAGE

Leaf:

*Arrangement.*—Distichous.

*Average length.*—Approximately 11.1 cm.

*Average width.*—Approximately 6.4 cm.

*Shape of blade.*—Obovate.

*Aspect.*—Horizontal.

*Apex.*—Unequal acute to unequal rounded.

*Base.*—Cuneate. Sheath length: Average 1.2 cm. Sheath width: Average 1.3 cm. Sheath color: Yellow-green; near RHS 144B.

*Margin.*—Entire.

*Texture of top surface.*—Smooth, moderately glossy, very slightly furrowed.

*Texture of bottom surface.*—Smooth, moderately glossy.

*Color.*—Young foliage upper side: Green to yellow-green; in between 137B and 146B. Young foliage under side: Yellow-green; in between 144A and 146C. Mature foliage upper side: Green to yellow-green; in between 137B and 146B. Mature foliage under side: Yellow-green; in between 144A and 146C.

*Venation.*—Type: Camptodromous. Venation coloration: upper side green; near 137B, under side same as leaf blade, yellow-green; in between near RHS-CC 144A and 146C.

Petiole: No petioles present.

FLOWERING CHARACTERISTICS

Flower bud:

*Rate of opening.*—Approximately 5 days after stage described.

*Length.*—Approximately 1.3 cm.

*Diameter.*—Approximately 1.2 cm wide and 1.4 cm high.

*Shape.*—Broad ovate.

*Color.*—Yellow-green to greyed-green; in between near RHS-CC 145D and 193A, heavily tinged greyed-purple; near RHS-CC 186D.

Peduncle:

*Length.*—Approximately 29.9 cm.

*Width.*—Approximately 0.5 cm.

*Aspect.*—Approximately 35° angle to vertical.

*Strength.*—Strong.

*Texture.*—Smooth, not very glossy.

*Color.*—Green; near RHS-CC 143A, heavily dotted and tinged greyed-purple; near RHS-CC N186A to N186B.

Inflorescence:

*Flowers per stem.*—Average 24.

*Inflorescence arrangement.*—Panicle.

*Inflorescence height.*—Approximately 18.0 cm (measured from lowest branching of panicle to top of inflorescence).

*Inflorescence width.*—Approximately 18.0 cm.

Individual flowers:

*Type.*—Single zygomorphic.

*Length (height).*—Approximately 3.9 cm.

*Width.*—Approximately 4.6 cm.

*Depth.*—Approximately 2.6 cm.

*Fragrance.*—No fragrance.

*Persistent.*—Non-persistent.

*Quantity of petals.*—2.

*Petals.*—Arrangement: One petal on each side of the column. Length: Approximately 2.3 cm. Width: Approximately 2.5 cm. Shape: Deltoid. Apex: Rounded. Base: Cuneate. Margin: Entire. Texture: Upper (forward) surface: smooth, dull, moderately velvety. Texture: Lower (back) surface: smooth, dull, moderately velvety. Color: When opening, forward surface: Purple to white; near 76C and NN155D, heavily, irregularly marbled purple; near N78A and N78B. When opening, back surface: Purple; near 76B and 76C, heavily irregularly marbled purple; near 77B and 77C, margin white; near NN155D. Fully Opened, forward surface: Purple to white; near 76C and NN155D, heavily irregularly marbled purple; near N78A and N78B. Fully Opened, back surface: Purple; near 76B and 76C, heavily irregularly marbled purple; near 77B and 77C, margin white; near NN155D. Fading, forward surface: Color does not fade, texture papery, no longer velvety. Fading, back surface: Color does not fade, texture papery, no longer velvety. Color Venation Fully Opened, forward surface: Purple; N78A. Fully Opened, back surface: Purple; near 77B.

*Labellum.*—Shape: Three-parted. Length: Approximately 2.0 cm. Width: Approximately 1.6 cm. Texture: Smooth, dull, slightly velvety. Tip: Cleft. Base: Cuneate. Color: When opening, forward surface: Central lobe red-purple; near N78, coloured red-purple towards the base; near 60A, with small yellow markings at the margins near the base; near 5B. Lateral lobes purple; near N78A, dotted red-purple at the base; near 71A, callosities yellow; near 4C, dotted red-purple; near 60A. When opening, back surface: Central lobe purple; near 76B, with small yellow markings at the margins near the base; near 4B, lateral lobes purple-violet; near N80C. Fully Opened, forward surface: Central lobe red-purple; near RHS-CC N78A, coloured red-purple towards the base; near 60A, with small yellow markings at the margins near the base; near 5B, lateral lobes purple; near N78B, dotted red-purple at the base; near 71A, callosities yellow; near 4C, dotted red-purple; near 60A. Fully Opened, back surface: Central lobe purple; near 76B, with small yellow markings at the margins near the base; near 4B, lateral lobes purple-violet; near N80D. Fading, forward surface: Color does not fade, texture papery, no longer velvety. Fading, back surface: Color does not fade, texture papery, no longer velvety. Color Venation Fully Opened, forward surface: No venation visible. Fully Opened, back surface: No venation visible. Margin: entire.

Sepals:

*Quantity.*—3.
*Appearance.*—Smooth, dull, moderately velvety.
*Length.*—Approximately 2.3 cm.
*Width.*—Approximately 1.8 cm.
*Shape.*—Ovate to obovate.
*Apex.*—Broad bluntly acute to obtuse.
*Base.*—Broad cuneate.
*Margin.*—Entire.
*Texture.*—Smooth, dull, moderately velvety.
*Color.*—Fully Opened, forward surface: Purple to white; a color between 76C and NN155D, heavily irregularly marbled purple; N78A and N78B. Fully Opened, back surface: Purple; near 76B heavily irregularly marbled purple; near 77B and 77C, margin white; near NN155D.

Pedicels:

*Length.*—Approximately 3.2 cm.
*Diameter.*—Approximately 0.3 cm.
*Angle.*—Approximately 85° to peduncle.
*Strength.*—Moderately strong.
*Texture.*—Smooth, moderately glossy.
*Color.*—Purple; near 75C, proximal part greyed-red; 182D.

REPRODUCTIVE ORGANS

*Stamens, style and stigma fused into column.*—Yes.
*Column length.*—Approximately 0.9 cm.
*Column diameter.*—Approximately 0.5 cm.
*Column color.*—Purple; near 76B and 77D, striped purple; near N78B.
*Ovary.*—Position: inferior. Diameter: Approximately 0.3 cm. Color: Purple; near 75C.
*Pollinia color.*—Yellow-orange; near RHS 17A and 17B.

OTHER CHARACTERISTICS

Disease resistance: Neither resistance nor susceptibility to the normal diseases found in *Phalaenopsis* has been observed.
Drought tolerance and cold tolerance: Normal for species.
Fruit/seed production: No fruits/seeds detected to date.

What is claimed is:

1. A new and distinct cultivar of *Phalaenopsis* plant named 'SUPHAL1109' as herein illustrated and described.

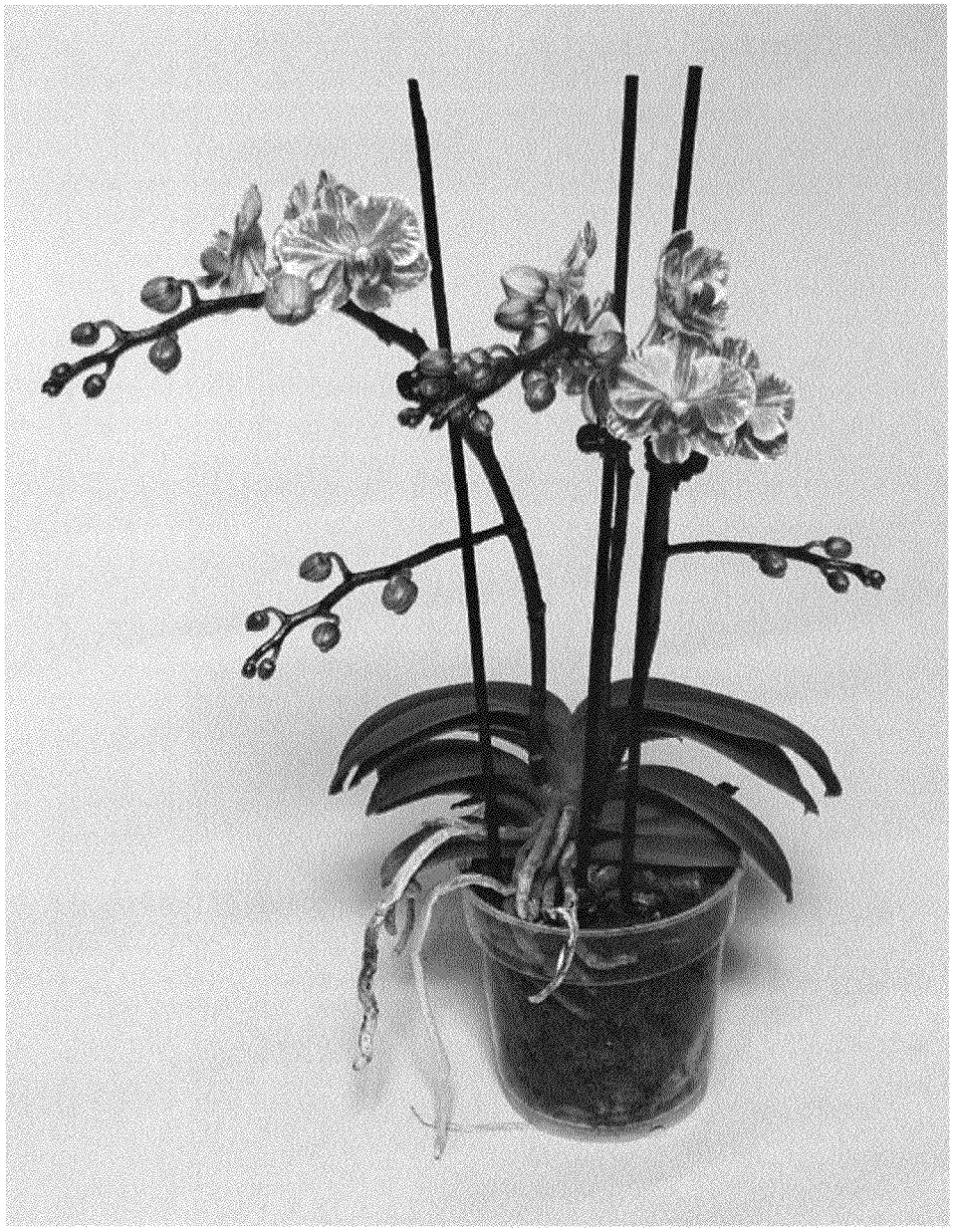

* * * * *